United States Patent [19]

Obermayer

[11] 4,324,558

[45] Apr. 13, 1982

[54] METHOD OF MONITORING TOXIC FLUIDS

[76] Inventor: Arthur S. Obermayer, 139 Main St., Cambridge, Mass. 02142

[21] Appl. No.: 245,339

[22] Filed: Mar. 19, 1981

Related U.S. Application Data

[62] Division of Ser. No. 62,973, Aug. 2, 1979, Pat. No. 4,258,000.

[51] Int. Cl.$^3$ ............................................. G01N 31/00
[52] U.S. Cl. ................................ 23/232 R; 23/230 M
[58] Field of Search ..................... 422/55, 56, 57, 58, 422/86, 87, 88; 116/206; 23/230 R, 232 R, 230 M; 73/27 R

[56] References Cited

U.S. PATENT DOCUMENTS

| | | | |
|---|---|---|---|
| 2,229,155 | 1/1941 | Wenker | 422/56 |
| 3,585,004 | 6/1971 | Mast | 422/56 |
| 3,635,679 | 1/1972 | Block et al. | 422/55 |
| 3,784,358 | 1/1974 | Drake, Jr. | 422/56 |
| 3,846,404 | 11/1974 | Nichols | 264/41 |
| 3,945,798 | 3/1976 | Young | 422/56 |
| 3,980,696 | 9/1976 | Anderson | 422/56 |
| 4,029,726 | 6/1977 | Nichols | 264/41 |
| 4,092,119 | 5/1978 | Baler et al. | 422/56 |

*Primary Examiner*—Frank W. Lutter
*Assistant Examiner*—Chris Konkol
*Attorney, Agent, or Firm*—Richard P. Crowley

[57] ABSTRACT

A toxic-monitoring material for the detecting and monitoring of toxic fluids placed in contact with or exposed to the monitoring material, which material comprises a solid, microporous, transparent, polymeric, matrix material having interconnecting micropores filled with a liquid composition, the liquid composition comprising a solvent for the toxic component to be detected and a reactant which reacts with the toxic component, whereby a toxic component dissolves in the solvent within the micropores and reacts with the reactant, to produce a change in color or appearance throughout the depth of the material, so that the detecting and monitoring of the toxic fluid may be determined.

22 Claims, No Drawings

METHOD OF MONITORING TOXIC FLUIDS

This is a division of application Ser. No. 62,973, filed Aug. 2, 1979, now U.S. Pat. No. 4,258,000, issued Mar. 24, 1981.

BACKGROUND OF THE INVENTION

Fluids in the work place and environment, particularly toxic vapors, may pose a significant hazard to personnel, and recent government health and safety regulations are focusing on such toxic liquids and vapors as a matter of concern. For example and typically, a large number of workers are being exposed routinely to toxic organic vapors, including halo hydrocarbons, benzene, vinyl chloride, acrylonitrile and toluene diisocyanate, which are often present in the work place and in the environment. Other gases which pose a health threat include industrial gases, such as phosgene, hydrogen cyanide, chlorine, formaldehyde and ammonia, and industrial contaminants, such as the oxides of sulfur, nitrogen and carbon, hydrogen sulfide and the like. There is no totally satisfactory method currently available to alert immediately an individual to overexposure to the hazards of toxic vapors, and, therefore, there is an urgent need to develop a toxic-vapor-monitoring, personnel badge for individual use which is convenient, rapid and specific in its response and is easy to interpret, is reliable and inexpensive.

In particular, a toxic-monitoring badge is desired which is subject to an immediate change as the concentration of toxic vapors varies, so that an individual, who may be desensitized by low-level toxic vapors in a nonhazardous concentration, may be alerted immediately by a rapid response when a high-level concentration of the vapor occurs, which would not be detected, for example, by subsequent instrumental analysis, such as in gaseous-contaminant dosimeters which contain means to inhibit convection movement of the diffused gases, such as those dosimeters described in U.S. Pat. Nos. 3,985,017 and 4,102,201.

Present, off-the-shelf, monitoring systems often are complex and bulky and require a back-up laboratory analysis to provide suitable results and often are expensive and time-consuming, requiring the use of fans, motors and power supplies. Other personnel dosimeters, such as the passive dosimeters, are unable to operate as a simple, clip-on badge, based on time-weighted averages, and do not function to warn a worker exposed to a toxic vapor at the real time of the hazard. Therefore, there exists a need for a simple, rapid, personnel, toxic badge element which can clearly display hazardous dose levels in a clearly visible manner and which is rapidly responsive to detect or monitor fluids on exposure or contact.

SUMMARY OF THE INVENTION

My invention concerns a toxic-fluid-monitoring material and a method of manufacturing and using such material, and in particular involves a transparent, liquid-impregnated, film material, wherein a liquid is maintained in a solid polymeric matrix, which material, on exposure to a vapor, preferentially provides for the dissolution of the vapor in the liquid material within the solid matrix and provides for a reaction within the solid matrix and the display of a color resulting from the reaction, so that exposure of the film material or contact with the toxic vapor provides for a rapid detecting and monitoring of the vapor.

The monitoring material of my invention comprises a solid matrix containing a liquid in which a specific color-producing chemical reaction can take place throughout the depth of the material. Therefore, the material should be a transparent and liquid-impregnated material in which the liquid is disposed in the micropores of the material. This liquid is adapted to allow rapid diffusion of a toxic component to which it is exposed and rapid reaction therewith to produce a change in appearance, particularly of color, as an indication of the detecting and monitoring of the toxic component to which the material is exposed.

Thus my material, employed in film, laminate, powder, fiber or other form, provides a mechanism by which the material can acquire vapor, conduct a color-producing reaction within the material, due to its liquid reactive reagents, and visually display the change in appearance or change in color due to such reaction, so that the individual is immediately and rapidly warned of exposure to a toxic liquid or gas. My material may be adopted and used in badge form, such as a clip-on film material fastened by a clasp to the clothing of an individual subject to exposure. The material may be used in detecting, monitoring or dosimetry. For example, if desired, it may be employed as a unique passive dosimeter badge which permits normal, solution-color producing chemistry to be performed within a solid, microporous, polymeric matrix. Because the liquid in the matrix has a high diffusion coefficient for solutes, it permits rapid chemical reactions between the toxic liquid or gas and the liquid reactant in the matrix. Further, the use of a variety of nonevaporative solvents, which are compatible with the polymeric matrix, permits long-time use in the environment. Further, the particular matrix employed is strong, inert, transparent, microporous, typically with interconnecting pores with average diameter of less than about 10 Micrometers, and more particularly less than 100 Angstroms; for example 10 to 100 Angstroms. Additionally, the matrix should be capable of holding a very high liquid content within the pores, in the most preferred embodiment, such as, for example, over 50% and typically 70% to 95% by volume. My material, particularly when employed in thin-film form, is transparent and signifies a change in appearance or color which is visible throughout the depth of the film material, which is distinct from other materials, such as paper, wherein a color change typically is solely on the surface of the paper and does not employ solution chemistry.

My toxic-fluid-monitoring material is useful for the monitoring of gases in the atmosphere in dosimeters and area mapping for health, safety and environmental uses. In addition to badges, it can be used in impinger tubes, in automated instrumental analysis systems, respirator end-of-life indicators and electronic alarms. Any gas or liquid may be detected which is capable of being diffused or captured by the liquid and of entering into a reaction which produces a color change, either through the formation of a precipitate, a dye, a complex, a compound or another means by which a change in color is induced within the material. The change in appearance may be a change between light and dark, or it may be a change in spectral properties preferably in the visible region, but alternatively in the ultraviolet or infrared region. Either a spectrophotometer, colorimeter or densitometer may be employed for quantitative measurement. The change also may be determined by fluorescence, electron-spin resonance or other instrumental methods.

The toxic-fluid-monitoring material of my invention comprises a transparent matrix material typically in film form, such as, for example, of less than 100 mils and typically less than 30 mils in thickness, with the matrix material preferentially an inert, polymeric material which is transparent or made transparent when filled with a liquid, and containing a plurality of micropores therein adapted to permit the retention of a high level of liquid therein. The monitoring material of my invention, therefore, comprises a solid, microporous, transparent, strong, inert, polymeric matrix which includes therein a liquid composition. The liquid composition comprises a solvent for the particular fluid component to be detected and monitored, so that the component is rapidly dissolved and distributed by diffusion throughout the body of the liquid-containing solid matrix. The liquid composition also includes a reactant compound with which the fluid component to be detected and monitored reacts or couples, and optionally may include an indicator means where the reaction, itself, is not indicative of the detecting and monitoring of the toxic fluid. The liquid composition may comprise any solution chemistry or mechanism which would detect and monitor the presence of the toxic liquid or gas through conventional solution-chemistry techniques, such as by the formation of a precipitate or a coupling reaction or a change in acidity or other means by which the appearance of the transparent, liquid-containing matrix is altered or wherein a change in color occurs, visible or invisible.

In use, the transparent, matrix, monitoring material, holding large quantities of liquid, is exposed to the toxic liquid or gas component which is dissolved in the solvent, and the component rapidly diffuses throughout the body of the matrix, while effecting at the same time a reaction resulting in a color change and an indication of exposure to the toxic liquid or gas. My toxic-monitoring material may be employed merely for the detecting of desired levels of the toxic fluid or the monitoring of the level of the toxic fluid or for dosimetry, providing for effective quantitative determination of toxic vapors, for example, at both the acute and chronic levels.

The change in appearance or the change in color of the transparent, monitoring, film material may be made visually or by instruments, may be made by face-viewing or, if desired, by edge-viewing techniques. The edge-viewing techniques require no special equipment and offer very high sensitivity. It is a direct consequence of the very high transparency of the matrix which permits transmission of light within the plane of a high liquid-content film. Both edge-viewing and face-viewing complement each other for the measurement of acute, single-time, exposure-limit values typically for a few minutes and chronic, time-weighted averages typically for 8 hours. The difference in optical-path length between the face view of a film and an edge view is generally about two orders of magnitude. This means that a given color level or intensity can be observed through the edge of the film, when the dose received is only about 1% of the integrated dose required for the same color through the face view.

A variety of microporous, matrix, polymeric materials may be employed, provided that the material as used is transparent and strong, has micropores and holds a sufficient amount of a liquid composition, so that the desired level of the toxic fluid may be detected, and so that a change is effected throughout the depth of the material, due to the liquid-filled, interconnecting micropores. For example, typical materials may include microporous olefinic materials, such as those materials known as Celgard, a microporous polypropylene resin material (a registered trademark of Celanese Corporation), or Tyvek, a microporous polyethylene material (a registered trademark of du Pont de Nemours Co.), both of which may be made transparent by the selection of a particular liquid composition.

The preferred matrix material, due to its very high liquid-level holding of over 70%, is the cellulose-triacetate-based material described and claimed in U.S. Pat. No. 3,846,404, issued Nov. 5, 1974, and cellulose-nitrate and other cellulosic-based materials described in U.S. Pat. No. 4,029,726, issued June 14, 1977, both patents hereby incorporated by reference in their entirety, and marketed and sold as Poroplastic material by Moleculon Research Corporation. The Poroplastic film material is particularly desirable, because it is strong, chemically inert and highly transparent when loaded with any of a wide variety of liquids. Such material may be composed of cellulose triacetate or cellulose nitrate; however, any polymeric or other matrix material may be used which is transparent and holds a high liquid content and which permits the chemical reaction to occur throughout the entire body of the matrix. The olefinic microporous materials are useful, but are not preferred, in that such materials at present are only capable of holding relatively lower levels of liquid compositions, such as, for example, over 20% to 30%.

The microporous, matrix, polymeric material may be transparent, per se, or may be made transparent by the selection of a particular liquid composition employed. The transparency should be sufficient to permit the change in coloration to be observed or to permit the measurement of change in color intensity. Transparency can be accomplished by the particular selection of the liquid composition within the micropores to be very similar to the index of refraction of the matrix material, so that, when the matrix material has its micropores filled with the selected liquid composition to effect the desired colorimetric reaction, the material in combination is transparent.

The liquid composition includes a liquid which is a solvent for the particular component of the toxic fluid to be detected and monitored. A wide variety of liquid solvents may be employed, depending upon the particular fluid component to be detected, but more typically the solvent should be a nonevaporative, relatively high-boiling solvent, so that it may be retained within the matrix and be employed as a badge or exposed to the environment over a long period of time without evaporation. The liquid solvent may be used alone or in combination with other solvents and typically may comprise water; alcohols, such as methanol, ethanol, isopropanol, decanol, ethylene glycol, propylene glycol, 1,5-pentanediol and polyethylene glycol; organic acids; amines; polyethers; esters; aliphatic and aromatic hydrocarbons; and combinations thereof. The liquid solvent selected, either alone or in combination, should not be such as to interfere with the desired color-producing reaction or component to be detected.

The liquid composition also may include an indicator, such as a typical acid-based indicator in a small, but effective amount sufficient so that, on the change of acidity, a color change is effected, or may contain other indicators, such as ultraviolet absorbers or the like, which would indicate or detect the presence of the toxic material or indicate the amount of the material through an optical change in the liquid composition.

The liquid composition also should include one or more reactants to provide for a reaction with the toxic component to be detected or monitored. The selection of the reactants should be such as to cause a change in appearance; for example, by producing a colored product or a precipitate within the micropores, or the reactant may be an indicator. Standard analytical chemistry techniques which produce a color may be employed. The use of standard solution chemistry permits the use of well-known analytical reactions and techniques to identify the toxic component of the fluid. The selection of any particular color-producing scheme can be based on such factors as the sensitivity required, the reagent or product stability, the compatability of the reagent with the solvent interference by other components with the toxic component to be monitored, the pH of the reaction, the reproducibility and reliability of the scheme, and the effect of humidity or heat. Although reactions preferably should take place to produce a color without the need for sequential and additional reactions, it is recognized that subsequent reaction steps may be desirable or necessary in order to produce a satisfactory colored product.

In use, my toxic-gas-monitoring material is able to acquire a gas and allow it to diffuse into the liquid, where a color-producing reaction occurs, and to display the resulting color reaction in a highly visible manner. The toxic vapor is acquired by diffusive acquisition typically in the form of a highly diluted gas in which the toxic component is present, typically in the range from 50 parts per million to 0.1 parts per million. In the absence of a mechanically driven circulation or other means, the only physical mechanism available for transferring toxic vapor to the active surface of the matrix is diffusion. For example, given a typical diffusion constant of about 0.1 $cm^2$/second, this would lead to the conclusion that about 10 picomoles of the gas vapor would enter each square centimeter of the absorbing film surface every second for every part per million of the toxic-vapor concentration. The toxic-vapor molecules pass into the solution and diffuse within the internal liquid phase of the matrix and subsequently become susceptible to and react with the reagents within the liquid composition.

As regards dose integration in the preferred form, the actual concentration of the color-reaction product in the matrix film material is simply proportional to the time integral of the vapor concentration to which the toxic-monitoring material of my invention has been exposed, which is usually a desirable characteristic. For quantitative measurements, the thickness of the diffusive boundary layer roughly should be constant over the period of integration, since, if the ambient airflow past the surface does vary substantially, it may be necessary to provide an artificial diffusive boundary layer; for example, the confined barrier may be used to provide for a stagnant-air layer over the film surface, such as, for example, in diffusive, passive-dosimeter badges. Of course, the reactive reagents within the micropores should not become exhausted during the particular integration time period selected; however, that is relatively easy to accomplish at low concentration levels. The color-producing reaction involved preferably should be irreversible, so that, when the toxic vapor is acquired, it is consumed and the color-reaction product is stable for a period sufficient to observe the reaction, or longer than the desired integration time, where a dose-integration mechanism is employed. Where the diffusive acquisition combines with a color-producing reaction to yield a concentration of a color-reaction product, which is proportional to the integrated dose of the toxic vapor, a visual display of the resulting color occurs when the light is viewed which has passed through some path within the film. Surprisingly, the proportionality of color or optical density with concentration can hold even when the color-reaction product is a precipitate, because the microporous structure prevents convection and allows the formation of more uniform-size particles. Thus, for example, a nickel dimethylglyoxime precipitate within the film produces a uniform, red color whose optical density is proportional to concentration. Thus, precipitates previously not appropriate for colorimetric quantitative analysis can be employed hereby for quantitative measurements.

In use, typically two limiting levels of coloration are recognized in importance, one of which is the threshold level where the color first becomes usefully perceptive to the eye or instrument, and the second of which is the saturation level where any further increase in optical density is not significant. Typically in an effective toxic-monitoring material of my invention, these two limits should correspond approximately to a small fraction of the 15-minute, single-time-exposure-limit (STEL) dose and some modest multiple of the maximum 8-hour, time-weighted-average (TWA) dose. For example, with the phosgene as a toxic gas, physical warning should be detected and be apparent after a 1-minute exposure, and thus the threshold for color appearance should be no greater than about 0.4 ppm minutes. Similarly, if government regulations permit an 8-hour exposure to a TWA level of 0.1 ppm of phosgene (amounting to 48 ppm minutes), effective badge-monitoring material should continue to provide reliable monitoring up to at least 150 ppm minutes. Thus the full range would range from about 0.4 to 150 ppm minutes and would define a total dose-integration range spanning a factor of 375, which is more than Beer's Law can provide to the eye under a single method of view. However, in employing both edge view and face view, which differ by a factor of about 100 in sensitivity, this represents an optical absorption range of from about 10% to 90%, well within the eye's discrimination. Thus the face and edge views can be applied to the same piece of film to offer coverage from about 0.8 ppm minutes to 2.0 ppm minutes for STEL and TWA coverage from about 8 ppm minutes to 200 ppm minutes.

My invention will be described for the purpose of illustration only in connection with certain specific and preferred embodiments. However, it is recognized and is within the skill of persons skilled in the art that various changes and modifications may be made to such examples, all of which are within the spirit and scope of my invention.

DESCRIPTION OF THE PREFERRED EMBODIMENTS

In connection with all of the experiments wherein a Poroplastic film material of cellulose triacetate is employed, the film had a thickness of approximately 0.1 to 0.3 mm, and the initial water content was 85% to about 90% by weight. Various aqueous reagents were introduced by simple immersive exchange of the large volume of reagent solution. Nonaqueous films were prepared by exchanging the initial water within the micropores of the film for isopropanol, and then the isopropanol for the desired final reaction solvent and then immersing in the actual reagent solution. All materials were compatible with the cellulose triacetate film, and the final dimensions and liquid contents were within a few percent of those of the initial valves.

EXAMPLE 1

Tollens' reagent for formaldehyde was made up from a 5% solution of silver nitrate which was made basic with a few drops of dilute sodium hydroxide. To this solution a 2% ammonia solution was added dropwise, until the precipitate of silver oxide just dissolved. This reagent was loaded into cellulose triacetate Poroplastic film by a diffusional exchange process, as set forth in U.S. Pat. No. 3,846,404, with the original water in the film ~85% to 90% by weight replaced with the Tollens' reagent. When the Tollens' reagent-loaded, transparent film was exposed to formaldehyde solution, a dark-brown precipitate formed within the film, and the film changed visually in appearance from transparent to a dark-brown, metallic luster appearance. The reaction can be used to monitor formaldehyde down to levels of 10 ppm. At a level of 1000 ppm, the reaction is rapid enough for an immediate response, but prolonged exposure (at least 40 minutes) to formaldehyde is necessary at 10 ppm.

EXAMPLE 2

A reagent for ammonia was made up of 50 mg of ethyl red indicator, 275 mg of 60% perchloric acid and 100 ml phenylethyl alcohol solvent. A piece of opaque, macroporous, polyethylene film (sold under the trademark Celgard 2402 by Celanese Corporation) was immediately dipped into the reagent solution, and excess reagent was blotted from the surface. The film material retained about 20% by weight of the reagent solution. Because of the similarity in refractive index between the polymer and the solvent, the resulting film became almost transparent. When this film was exposed to ammonia gas, it turned from colorless to scarlet red, with the first observable color appearance occurring in approximately 3 minutes. The color intensity was dependent on the ammonia concentration, and low color intensity was due to the low liquid content of the reagent in the film. Repetition of this experiment was also successfully carried out using a porous polypropylene film material (sold as Tyvek by du Pont de Nemours Co.).

EXAMPLE 3

A reagent for phosgene was made up by dissolving 1% nitrobenzylpyridine and 2% phenylbenzylamine in a solvent made up of equal parts of diethyl phthalate and sebaconitrile. This reagent solution was loaded into cellulose triacetate Poroplastic film by a diffusional exchange process, as in Example 1. When the film was exposed to phosgene gas, the direct, face, threshold, color perception level was 0.5 ppm minutes and the edge-on value was less than 0.05 ppm. Upon exposure to 50 ppm minutes, the two methods of observation gave a deep scarlet color and complete opacity, respectively.

These experiments were repeated using a Beckman DB Spectrometer to measure absorbance at 475 nm. These showed an increase in absorbance ($\log_{10} 1/1$) of 0.025 per ppmm of integrated dose. Assuming a threshold color perception at 5% absorption at $\lambda$ max and color saturation at 95% absorption, this instrumental calibration constant predicts visual threshold and saturation exposures of 0.9 ppmm and 52 ppmm, which is in good agreement with the actual direct-view, visual estimate.

EXAMPLE 4

Other examples were carried out employing as the polymeric matrix a reagent, liquid-loaded, cellulose triacetate film (Poroplastic), using the following:

| Indicator | Solvent | Fluid to be monitored | Color change |
|---|---|---|---|
| Alizerin Red S | Polyethylene Glycol 200 | $NH_3$ gas | yellow to violet |
| Bromophenol Blue with Di(2-ethylhexyl) phosphoric acid | Polyethylene Glycol 400 | $NH_3$ gas | colorless to blue |
| Ferric ion/MBTH | Water | $CH_2O$ gas | colorless to blue |
| Dimethylglyoxime | 1,4 butanediol | Nickelous salt solution | colorless* to red |
| Lead acetate | 1,5-pentanediol | $H_2S$ gas | colorless to dark brown |

*two-step process with two film layers

What I claim is:
1. A method of detecting a toxic fluid, which method comprises:
   (a) providing a material for the detecting and monitoring of a toxic fluid, which material comprises a solid, microporous, transparent, polymeric, matrix material having interconnecting micropores, the micropores being of sufficiently small size or of index-matching polymeric composition to permit the material to be transparent or be made transparent, when the micropores contain a liquid composition, and which micropores permit a high solute-liquid diffusion coefficient, and which matrix material includes, within the interconnecting small micropores, a liquid composition, which liquid composition is nonreactive with the polymeric matrix material and which is retained within the interconnecting pores of the matrix material in a volume greater than 20% by volume of the polymeric matrix material, and which liquid composition comprises
      (i) a nonevaporative solvent for the toxic fluid to be detected, whereby the fluid will be dissolved rapidly in the solvent, on exposure of the badge-monitoring material to the toxic fluid, and
      (ii) a reactant for the toxic fluid dissolved in the solvent which reacts with the toxic fluid and which, on such reaction, results or causes a change in visual appearance of the liquid composition maintained within the micropores of the matrix material, whereby a rapid, diffusive change in the appearance of the transparent matrix material appears throughout the depth of the matrix material which signals and detects the presence of the toxic fluid to which the matrix material has been exposed;
   (b) exposing the toxic fluid, whose presence is to be detected, to the liquid-filled matrix material; and
   (c) observing a change in appearance of the liquid-composition-filled matrix material, after exposure of the material, over a predetermined time period, to the toxic fluid, thereby detecting the presence of a toxic fluid.

2. The method of claim 1 wherein the matrix material is in the form of a thin-film material having a film thickness of less than 0.8 mm in thickness.

3. The method of claim 1 wherein the interconnecting micropores of the matrix material have an average diameter of less than about 10 micrometers.

4. The method of claim 3 wherein the interconnecting micropores have an average diameter ranging from about 10 to 100 Angstroms.

5. The method of claim 1 wherein the polymeric matrix material is selected from the group consisting of cellulose triacetate, cellulose nitrate and polyolefinic $C_2$–$C_4$ polymeric material.

6. The method of claim 1 wherein the solvent comprises a nonevaporative liquid material selected from the group consisting of water, alcohols, polyols, esters, ethers, hydrocarbons and combinations thereof.

7. The method of claim 1 wherein the liquid composition disposed in the micropores of the matrix material includes a small but effective amount of an indicator which is subject to a change in appearance, on exposure of the matrix material to the toxic fluid.

8. The method of claim 7 wherein the indicator comprises a pH indicator which changes color responsive to the reaction of the reactant with the component of the toxic fluid to which the matrix material is exposed.

9. The method of claim 1 wherein the reactant is a compound which reacts with the component of the toxic fluid to which the matrix material is exposed, to produce a precipitate in the liquid composition, which precipitate changes the color appearance throughout the depth of the matrix material, to indicate and to detect the presence of the toxic fluid.

10. The method of claim 1 wherein the liquid composition has a refractive index similar to that of the polymeric matrix material, to provide for a transparent, toxic-monitoring material.

11. The method of claim 1 wherein the liquid composition comprises from about 70% to 95% by volume of the total toxic-monitoring material, and the toxic-monitoring material is in the form of a transparent film material.

12. The method of claim 1 which includes a material in thin-film form, which thin film is secured and supported on one surface to a supporting sheet material.

13. The method of claim 12 wherein the supporting sheet material comprises a solid, transparent, polymeric sheet material secured to at least one surface of the matrix material.

14. The method of claim 1 wherein the toxic fluid comprises a liquid, which liquid is placed in direct contact with the liquid-filled matrix material.

15. The method of claim 1 wherein the toxic fluid is dissolved in the solvent material within the micropores of the matrix material.

16. The method of claim 1 wherein the toxic fluid comprises a liquid solution of formaldehyde.

17. The method of claim 1 which includes determining the extent of the change in appearance of the transparent material before and after exposure, to determine the quantity of toxic component to which the liquid-filled matrix material has been exposed.

18. The method of claim 1 wherein the liquid composition in the micropores includes an indicator, and which method includes observing the change in color of the indicator in the liquid composition, to determine the presence of a toxic fluid to which the matrix material has been exposed, said use which includes selecting as the liquid composition within the micropores a liquid composition which has a refractive index similar to the refractive index of the polymeric matrix material.

19. The method of claim 1 wherein the liquid composition comprises a water solution of a Tollens' reagent in the micropores, and which method includes exposing the liquid-filled matrix material to formaldehyde and detecting the presence of formaldehyde.

20. The method of claim 1, which method includes visually observing the face area of the material for a change in color.

21. The method of claim 1 wherein the material is in thin-film form, and which includes observing the amount and nature of the change in color by observation of the opposite end edges of the film material.

22. The method of claim 1, which method includes measuring by an instrument the quantitative measurement of the change in visual appearance.

* * * * *